(12) United States Patent (10) Patent No.: US 7,939,090 B2
Wheeler et al. (45) Date of Patent: May 10, 2011

(54) SYSTEM AND METHOD FOR THE TREATMENT OF CANCER, INCLUDING CANCERS OF THE CENTRAL NERVOUS SYSTEM

(75) Inventors: Christopher Wheeler, Newbury Park, CA (US); Asha Das, Los Angeles, CA (US); Keith L. Black, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 10/575,438

(22) PCT Filed: Oct. 20, 2004

(86) PCT No.: PCT/US2004/034761
§ 371 (c)(1),
(2), (4) Date: Apr. 11, 2006

(87) PCT Pub. No.: WO2005/043155
PCT Pub. Date: May 12, 2005

(65) Prior Publication Data
US 2007/0020297 A1 Jan. 25, 2007

Related U.S. Application Data

(60) Provisional application No. 60/513,040, filed on Oct. 21, 2003.

(51) Int. Cl.
*A61K 39/00* (2006.01)
(52) U.S. Cl. .................................................. 424/277.1
(58) Field of Classification Search .................... None
See application file for complete search history.

(56) References Cited

U.S. PATENT DOCUMENTS

| | | | |
|---|---|---|---|
| 5,643,786 A | 7/1997 | Cohen et al. | |
| 5,788,963 A | 8/1998 | Murphy et al. | |
| 5,849,589 A | 12/1998 | Tedder et al. | |
| 5,851,756 A | 12/1998 | Steinman et al. | |
| 5,994,126 A | 11/1999 | Steinman et al. | |
| 6,010,905 A | 1/2000 | Cohen | |
| 6,037,135 A | 3/2000 | Kubo et al. | |
| 6,077,519 A | 6/2000 | Storkus et al. | |
| 6,458,585 B1 | 10/2002 | Vachula et al. | |
| 6,479,286 B1 | 11/2002 | Nelson et al. | |
| 6,482,405 B1 | 11/2002 | Tahara et al. | |
| 6,514,942 B1 | 2/2003 | Ioannides et al. | |
| 6,537,560 B1 | 3/2003 | Kawakami et al. | |
| 6,566,395 B1 | 5/2003 | Moran | |
| 6,632,459 B2 | 10/2003 | Graus et al. | |
| 7,247,480 B2 | 7/2007 | Waldmann et al. | |
| 7,338,929 B2 | 3/2008 | Debinski et al. | |
| 2002/0034819 A1 | 3/2002 | Smith et al. | |
| 2002/0119121 A1* | 8/2002 | Vitiello et al. | 424/85.2 |
| 2002/0192211 A1 | 12/2002 | Hudziak et al. | |
| 2003/0095955 A1 | 5/2003 | Noessner et al. | |
| 2003/0185823 A1 | 10/2003 | Lum et al. | |
| 2003/0190682 A1 | 10/2003 | Law et al. | |
| 2003/0202963 A1 | 10/2003 | Crystal et al. | |
| 2004/0057935 A1* | 3/2004 | Yu et al. | 424/93.7 |
| 2004/0072246 A1 | 4/2004 | Martin et al. | |
| 2004/0197903 A1 | 10/2004 | Pestano | |
| 2004/0203143 A1 | 10/2004 | Tjoa et al. | |
| 2005/0059151 A1 | 3/2005 | Bosch | |
| 2006/0204509 A1 | 9/2006 | Harty et al. | |
| 2007/0098776 A1 | 5/2007 | Fikes et al. | |
| 2007/0167375 A1 | 7/2007 | Okada et al. | |
| 2008/0107668 A1 | 5/2008 | Philip et al. | |
| 2008/0199484 A1 | 8/2008 | Yu et al. | |
| 2008/0206286 A1 | 8/2008 | Yu | |
| 2008/0311141 A1 | 12/2008 | Yu et al. | |
| 2008/0311142 A1 | 12/2008 | Yu et al. | |

FOREIGN PATENT DOCUMENTS

| | | |
|---|---|---|
| WO | WO 89/06692 | 7/1989 |
| WO | WO 94/26293 | 11/1994 |
| WO | WO 95/21862 | 8/1995 |
| WO | WO 96/18409 | 6/1996 |
| WO | WO 00/24778 | 5/2000 |
| WO | WO 00/38730 | 7/2000 |
| WO | WO 01/08636 | 2/2001 |
| WO | WO 01/41741 | 6/2001 |
| WO | WO 02/11742 | 2/2002 |
| WO | WO 02/068474 | 9/2002 |
| WO | WO 03/010301 | 2/2003 |
| WO | WO 03/014335 | 2/2003 |
| WO | WO 03/035004 | 5/2003 |
| WO | WO 2005/037995 | 4/2005 |
| WO | WO 2005/079581 | 9/2005 |
| WO | WO 2008/039874 | 4/2008 |
| WO | WO 2008/039969 | 4/2008 |
| WO | WO 2008/039974 | 4/2008 |

OTHER PUBLICATIONS

Tong et al (Cancer Research, 2001, 61:7530-7535.* Yu et al I (Cancer Research, 2001, 61:842-847, IDS).*
Friedman et al (Clinical Cancer Research, 2000, 6:2585-2597).*
Liu et al (J of Immunotherapy, Jul./Aug. 2003, 26:301-312).*
Knutson (Current Opinion in Molecular Therapeutics, Aug. 2002, 4:403-407).*
Osada et al (Jpn J Clinical Oncology, 2001, 31:403-406).*
Kikuchi et al (Cancer Immunol Immunother, 2001, 50:337-344).*
Zhang et al (Clinical Cancer Research, 2007, 13:566-575).*
Merrick et al (Cancer Immunol Immunother, 2008, 57:897-906).*
Okada et al (Int J Cancer, 1998, 78:196-201).*
Liau et al (J Neurosurgery, 1999, 90:1115-1124).*
Heimberger et al (J of Neuroimmunology, 2000, 103:16-25).*

(Continued)

*Primary Examiner* — Laura B Goddard
(74) *Attorney, Agent, or Firm* — Fish & Richardson P.C.

(57) ABSTRACT

The invention relates to the treatment of cancer, and particularly to the treatment of cancers of the central nervous system, such as glioblastoma multiforme. A dual therapeutic approach is provided, including the administration of a dendritic cell-based cancer vaccine and a regimen of chemotherapy. The two therapies may be administered concurrently with one another and/or with an initial vaccination preceding chemotherapy. In various embodiments, the dendritic cell-based cancer vaccine includes either primed or unprimed dendritic cells; for instance, the dendritic cells may be autologous tumor antigen-presented dendritic cells. The dual therapeutic approach of the instant invention beneficially influences the chemosensitivity of a mammal with cancer.

12 Claims, 5 Drawing Sheets

OTHER PUBLICATIONS

Shin et al, Antitumor Effect of Intratumoral Administration of Dendrite Cell Combination With Vincristine Chemotherapy in a Murine Fabrosarcoma Model, Histology and Histopathology, Apr. 2003, pp. 435-447, 18:2.

Yu et al., Effective Combination of Chemotherapy and Dendritic Cell Administration for the Treatment of Advanced-Stage Experimental Breast Cancer, Clinical Cancer Research, Jan. 2003, pp. 285-294, 9:1.

Tanaka et al., Intratumoral Injection of Dendritic Cells After Treatment of Anticancer Drugs Induces Tumor-Specific Antitumor Effect in Vivo, International Journal of Cancer, Sep. 20, 2002, pp. 265-269, 101:3.

Ghosh et al., Dendrite Cell-Based Immunotherapy Combined With Antimony-Based Chemotherapy Cures Established Murine Visceral Leishmanlasis, The Journal of Immunology, Jun. 1, 2003, pp. 5625-5629, 170:11.

Inoue et al., Dendrite Cell Coinjected With Tumor Cells Treated With an Anticancer Drug to Induce Tumor Rejection, Surgery Today, Apr. 4, 2003, pp. 269-276, 33:4.

Reichardt et al., Idiotype Vaccination of Multiple Meyloma Patients Using Monocyte-Derived Dendritic Cells, Haematologica, Oct. 2003, pp. 1139-1149, 88:10.

Chui et al., Dendrite Cell Vaccination Following High Dose Chemotherapy With Autologous Stem Cell Support for Breast Cancer. Long-Term Follow-Up, Proceedings of the American Society of Clinical Oncology, Jun. 2003, 22 (Abstract Only).

Castro et al., Current and Future Strategies for the Treatment of Malignant Brain Tumors, Pharmacology & Therapeutics, Apr. 2003, pp. 71-108, 98:1.

Pollack et al., Exploitation of Immune Machanisms in the Treatment of Central Nervous System Cancer, Seminars in Pediatric Neurology, Jun. 2000, pp. 131-143, 7:2.

Yu et al., Vaccination of Malignant Morrie Patients With Peptide-Pulsed Dendritic Cells Elicits Systemic Cytotoxicity and Intracranial T-Cell Infiltration, Cancer Research, Feb. 1, 2001, pp. 842-847, 61:3.

Steinman, R.M., Some Interfaces of Dendritic Cell Biology, Acta Pathologica, Microbiologica, et Immunologica Scandinavica, Jul. 2003, pp. 675-897, 111:7-8.

Bowles, Jr. et al., "Long-term Remission of Malignant Brain Tumors after Intracranial Infection: A Report of Four Cases," Neurosurgery, vol. 44: 636-642 (1999).

Chandler et al., "Long-Term Survival in Patients with Glioblastoma Multiforme," Neurosurgery, vol. 32:716-720 (1993).

Curran et al., "Recursive Partitioning Analysis of Prognostic Factors in Three Radiation Therapy Oncology Group Malignant Glioma Trials," J Natl Cancer Inst, vol. 85:704-710 (1993).

Liau et al., "Treatment of intracranial gliomas with bone marrow-derived dendritic cells pulsed with tumor antigens," J Neurosurg, vol. 90:1115-1124 (1999).

Okada et al., "Autologous glioma cell vaccine admixed with interleukin-4 gene transfected fibroblasts in the treatment of recurrent glioblastoma: preliminary observations in a patient with a favorable response to therapy," Journal of Neuro-Oncology, vol. 64:13-20 (2003).

Stupp et al., "Recent Developments in the Management of Malignant Glioma," American Society of Clinical Oncology Educational Book, 779-788 (2003).

Wheeler et al., "Thymic $CD8^+$ T Cell Production Strongly Influences Tumor Antigen Recognition and Age-Dependent Glioma Mortality," The Journal of Immunology, vol. 171:4927-4933 (2003).

Wheeler et al., "Clinical responsiveness of glioblastoma multiforme to chemotherapy after vaccination," Clin. Cancer Res., 10:5316-26 (2004).

Wheeler et al., "Vaccination elicits correlated immune and clinical responses in glioblastoma multiforme patients," Cancer Res., 68:5955-64 (2008).

Kikuchi et al., "Intratumoral injection of dendritic and irradiated glioma cells induces anti-tumor effects in a mouse brain tumor model," Cancer Immunol. Immumother., 51:424-430 (2002).

Liu et al., "Cytotoxic T cell targeting of TRP-2 sensitizes human malignant glioma to chemotherapy," Oncogene, 24:5226-34 (2005).

Liu et al., "Sensitization of malignant glioma to chemotherapy through dendritic cell vaccination," Expert Rev. Vaccines, 5:233-247 (2006).

Nowak et al., "Synergy between chemotherapy and immunotherapy in the treatment of established murine solid tumors," Cancer Res., 63:4490-96 (2003).

Song et al., "Strategies to improve dendritic cell-based immunotherapy against cancer," Yonsei Med. J., 45(Suppl):48-52 (2004).

Yu et al., "Mahaley Clinical Research Award: chemosensitization of glioma through dendritic cell vaccination," Clin. Neurosurg., 53:345-351 (2006).

Abdel-Wahab et al., "Human dendritic cells, pulsed with either melanoma tumor cell lysates or the gp100 peptide(280-288), induce pairs of T-cell cultures with similar phenotype and lytic activity," Cell. Immunol., 186:63-74 (1998).

Akasaki et al., "Antitumor effect of immunizations with fusions of dendritic and glioma cells in a mouse brain tumor model," J. Immunother., 24:106-113 (2001).

Akasaki et al., "Dendritic cell-based immunotherapy for malignant gliomas," Expert Rev. Neurother., 5:497-508 (2005).

Akasaki et al., "Induction of a CD4+ T regulatory type 1 response by cyclooxygenase-2-overexpressing glioma," J. Immunol., 173:4352-59 (2004).

Akasaki et al., "T cell immunity in patients with malignant glioma: recent progress in dendritic cell-based immunotherapeutic approaches," Front. Biosci., 10:2908-21 (2005).

Candido et al., "Local administration of dendritic cells inhibits established breast tumor growth: implications for apoptosis-inducing agents," Cancer Res., 61:228-236 (2001).

Casey et al., "Heat shock protein derived from a non-autologous tumour can be used as an anti-tumour vaccine," Immunology, 110:105-111 (2003).

Dietz, "Engineering dendritic cell grafts for clinical trials in cellular immunotherapy of cancer: example of chronic myelogenous leukemia," Croatian Med. J., 42:428-435 (2001).

Ehtesham et al., "Intratumoral dendritic cell vaccination elicits potent tumoricidal immunity against malignant glioma in rats," J. Immunother., 26:107-116 (2003).

Ehtesham et al., "Recent progress in immunotherapy for malignant glioma: treatment strategies and results from clinical trials," Cancer Control, 11:192-207 (2004).

Gatza et al., "Tumor cell lysate-pulsed dendritic cells are more effective than TCR Id protein vaccines for active immunotherapy of T cell lymphoma," J. Immunol., 169:5227-35 (2002).

Geiger et al., "Vaccination of pediatric solid tumor patients with tumor lysate-pulsed dendritic cells can expand specific T cells and mediate tumor regression," Cancer Res., 61:8513-19 (2001).

Gilboa et al., "Immunotherapy of cancer with dendritic-cell-based vaccines," Cancer Immunol. Immunother., 46:82-87 (1998).

Hirschmann-Jax et al., "A distinct 'side population' of cells with high drug efflux capacity in human tumor cells," Proc. Natl. Acad. Sci. USA, 39:14228-33 (2004).

Liu et al., "Cancer vaccines: a novel strategy to sensitize malignant glioma to chemotherapy," Expert Rev. Neurother., 7:1235-37 (2007).

Liu et al., "Cell-mediated immunotherapy: a new approach to the treatment of malignant glioma," Cancer Control, 10:138-147 (2003).

Liu et al., "HER-2, gp100, and MAGE-1 are expressed in human glioblastoma and recognized by cytotoxic T cells," Cancer Res., 64:4980-86 (2004).

Liu et al., "Small interference RNA modulation of IL-10 in human monocyte-derived dendritic cells enhances the Th1 response," Eur. J. Immunol., 34:1680-87 (2004).

Luptrawan et al., "Dendritic cell immunotherapy for malignant gliomas," Rev. Recent Clin. Trials, 3:10-21 (2008).

Mehta-Damani et al., "Generation of antigen-specific CD4+ T cell lines from naïve precursors," Eur. J. Immunol., 5:1206-11 (1995).

Mehta-Damani et al., "Generation of antigen-specific CD8+ CTLs from naïve precursors," J. Immunol., 153:996-1003 (1994).

Melcher et al., "Dendritic cells for the immunotherapy of cancer," Clin. Oncol., 14:185-192 (2002).

Mi et al., "Induced apoptosis supports spread of adenovirus rectors in tumors," Hum. Gene Ther., 12:1343-52 (2001).

Parmiani et al., "Cancer immunotherapy with peptide-based vaccines: What have we achieved? Where are we going?" J. Natl. Cancer Inst., 94:805-818 (2002).

Rissoan et al., "Reciprocal control of T helper cell and dendritic cell differentiation," Science, 283:1183-86 (1999).

Song et al., "Strategies to improve dendritic cell-based immunotherapy against cancer," Yonsei Med. J., 45(Suppl):48-52 (2004).

Steinbrink et al., "CD4+ and CD8+ anergic T cells induced by interleukin-10-treated human dendritic cells display antigen-specific suppressor activity," Blood, 99:2468-76 (2002).

Takagi et al., "Anti-tumor effects of dendritic and tumor cell fusions are not dependent on expression of MHC class I and II by dendritic cells," Cancer Lett., 213:49-55 (2004).

Wheeler et al., "Cellular immunity in the treatment of brain tumors," Clin. Neurosurg., 51:132-139 (2004).

Yamazaki et al., "Direct expansion of functional CD25+ CD4+ regulatory T cells by antigen-processing dendritic cells," J. Exp. Med., 198:235-247 (2003).

Young et al., "Dendritic cells stimulate primary human cytolytic lymphocyte responses in the absence of CD4+ helper T cells," J. Exp. Med., 171:1315-32 (1990).

Yu et al., "Vaccination with tumor lysate-pulsed dendritic cells elicits antigen-specific, cytotoxic T-cells in patients with malignant glioma," Cancer Res., 64:4973-79 (2004).

Zitvogel et al., "Therapy of murine tumors with tumor peptide-pulsed dendritic cells: dependence on T cells, B7 costimulation, and T helper cell-1 associated cytokines," J. Exp. Med., 183:87-97 (1996).

Soling et al., "Dendritic cell therapy of primary brain tumors," Mol. Med., 7:659-667 (2001).

European Examiner Oskar Lechner, Communication for Application No. EP 04795865.7, dated Oct. 4, 2010, 7 pages.

\* cited by examiner

Figure 5

|  | Vaccine | Chemotherapy | Vaccine + Chemotherapy | Significance (p) |
|---|---|---|---|---|
| Age | 53.4 ± 13 | 55.7 ± 10 | 54.0 ± 10 | 0.88 * |
| Post-vaccine Karnofsky Score | 84 ± 16 | - | 93 ± 9 | 0.12 * |
| % male | 50 | 38 | 77 | 0.14 † |
| % non-survivors | 100 | 92 | 77 | 0.3 † |
| % > 2 surgeries before vaccine | 58.3 | - | 61.5 | 0.43 † |
| % no chemo before vaccine | 66.7 | - | 61.5 | 0.58 † |
| % no surgery after vaccine | 58.3 | - | 53.8 | 1.0 † |
| Days from surgery to vaccine | 115 ± 14 | - | 121 ± 13 | 0.94 ¶ |
| Mean survival (months) | 17.9 ± 1.7 | 15.9 ± 2.1 | 26 ± 3.7 | 0.047 ¶ |
| % 2-year survival (fraction) | 8.3 (1/12) | 8.3 (1/12) | 41.7 (5/12) | > 0.05 †; < 0.05 ** |
| % 3-year survival (fraction) | 0 (0/12) | 0 (0/12) | 18.2 (2/11) | > 0.05 †; < 0.01 ** |

¹Statistical methods: * ANOVA; † Fisher's Exact Test; ¶ Log-rank; ** Binomial distribution. Calculations of % 2- and 3-year survival excluded censored values.

Figure 6

|  | Phase IA | Phase IB | Phase II |
|---|---|---|---|
| Vaccine | 7 pts | 3 pts | 2 pts |
| Vaccine + chemotherapy | 1 pts | 2 pts | 10 pts |
| Antigen source | Tumor line MHC I-elution | Tumor lysate | Tumor lysate |
| Vaccine course | 3; 2 wks apart | 3; 2 wks apart | 3; 2 wks apart + 1; 6 wks later |
| Eligibility Diagnosis | de novo GBM, de novo AA | de novo or recurrent GBM, AA | de novo or recurrent GBM, AA |
| Karnofsky score | ≥ 60 | ≥ 60 | ≥ 60 |
| Age | ≥ 18 yr | ≥ 18 yr | ≥ 18 yr |
| CTL Responsiveness (GBM only) | 60% * | 60% †¶ | 40% ¶ |

¹CTL responsiveness was determined from 5 testable samples per trial: * Bulk CTL assay; † Elispot; ¶ IFN-γ production by qPCR.

Figure 7

| Vaccine + Chemotherapy | Pt # | Drug(s) |
|---|---|---|
| | 1 | Gliadel wafers |
| | 2 | Temozolamide |
| | 3 | Temozolamide |
| | 4 | Temozolamide |
| | 5 | Temozolamide, Irinotecan |
| | 6 | Temozolamide |
| | 7 | Temozolamide, Accutane |
| | 8 | Tamoxifen |
| | 9 | Temozolamide, CCNU |
| | 10 | Temozolamide, Accutane |
| | 11 | Temozolamide, Gleevec |
| | 12 | Temozolamide, Procarbazine, CCNU, Vincristine |
| | 13 | Temozolamide, Thalidomide, Etoposide |
| Chemotherapy | | |
| | 1 | Temozolamide |
| | 2 | Temozolamide |
| | 3 | Temozolamide, Procarbazine |
| | 4 | Temozolamide, Carboplatin, Vincristine, Procarbazine |
| | 5 | Temozolamide, BCNU, Thalidomide |
| | 6 | Temozolamide, Procarbazine |
| | 7 | Temozolamide |
| | 8 | Temozolamide, Thalidomide |
| | 9 | Gliadel wafers, Vincristine |
| | 10 | Temozolamide, Carboplatin, Vincristine |
| | 11 | BCNU, Temozolamide |
| | 12 | Gliadel wafers, Temozolamide |
| | 13 | BCNU |

SEQUENCE LISTING

<160> NUMBER OF SEQ ID NOS: 3

<210> SEQ ID NO 1
<211> LENGTH: 21
<212> TYPE: DNA
<213> ORGANISM: Artificial
<220> FEATURE:
<223> OTHER INFORMATION: PCR Primer

<400> SEQUENCE: 1

-continued

```
cacatccctt tcaaccatgc t                                        21

<210> SEQ ID NO 2
<211> LENGTH: 19
<212> TYPE: DNA
<213> ORGANISM: Artificial
<220> FEATURE:
<223> OTHER INFORMATION: PCR Primer

<400> SEQUENCE: 2
gccagctgca gggtttagg                                           19

<210> SEQ ID NO 3
<211> LENGTH: 30
<212> TYPE: DNA
<213> ORGANISM: Artificial
<220> FEATURE:
<223> OTHER INFORMATION: 5' FAM/3' TAMRA Probe

<400> SEQUENCE: 3
acacctctgg ttttgtaaa ggtgcccact                                30
```

SYSTEM AND METHOD FOR THE TREATMENT OF CANCER, INCLUDING CANCERS OF THE CENTRAL NERVOUS SYSTEM

This application is the National Phase of International Application PCT/US04/34761, filed Oct. 20, 2004, which designated the U.S. and that International Application was published under PCT Article 21(2) in English. This application also includes a claim of priority under 35 U.S.C. §119(e) to U.S. provisional patent application No. 60/513,040, filed Oct. 21, 2003.

BACKGROUND OF THE INVENTION

1. Field of the Invention

The invention relates to the treatment of cancer, and in particular embodiments to cancers of the central nervous system ("CNS"), such as those found in the brain.

2. Description of Related Art

Malignant brain tumors are among the gravest forms of cancer. The most common of these incurable tumors, glioblastoma multiforme ("GBM"), is responsible for 50% of all intracranial gliomas and 25% of intracranial tumors in adults. See, e.g., L. M. DeAngelis, "Medical progress: Brain tumors," *N. Engl. J. Med.*, 344:114 (2001); and F. G. Davis et al., "Prevalence estimates for primary brain tumors in the United States by behavior and major histology groups," *Neuro-oncol.* 3:152 (2001). GBM diagnosis carries with it an average survival between twelve and eighteen months (with 90-95% patients surviving less than two years), without the possibility of spontaneous remission or effective treatment. See, e.g. Id.; and W. J. J. Curran et al., "Recursive partitioning analysis of prognostic factors in three Radiation Therapy Oncology Group malignant glioma trials," *J. Natl. Cancer Inst.*, 85:690 (1993). The consistently short survival and absence of spontaneous remission that makes GBM such a devastating disease also renders the evaluation of new therapies for this disease relatively rapid and unequivocal. Overall survival represents the standard by which therapies for GBM are evaluated, in part because tumor mass reduction (i.e., surgically) does not necessarily correlate with prolonged survival. See, e.g., F. W. Kreth et a., "Surgical resection and radiation therapy versus biopsy and radiation therapy in the treatment of glioblastoma multiforme," *J. Neurosurg.*, 78:762 (1993); M. R. Quigley et al., "Value of surgical intervention in the treatment of glioma," *Stereotact. Funct. Neurosurg.*, 65:171 (1995); and S. J. Hentschel et al., "Current surgical management of glioblastoma," *Cancer J.*, 9:113 (2003).

Unfortunately, conventional therapies are remarkably ineffective at improving GBM clinical outcome, despite their ability to confer significant benefits to patients with non-glioma tumors. See, e.g., Curran at 690; J. F. Reavey-Cantwell et al., "The prognostic value of tumor markers in patients with glioblastoma multiforme: analysis of 32 patients and review of the literature," *J. Neurooncol.*, 55:195 (2001); and R. Stupp et al., "Recent developments in the management of malignant glioma," *J. Clin. Oncol.*, 1091-9118:779 (2001). Even the few treatments effective against GBM typically either exhibit small increases in survival that are evident only from large population studies, or primarily benefit certain (i.e., young) patient subpopulations. See, e.g., H. A. Fine et al., "Meta-analysis of radiation therapy with and without adjuvant chemotherapy for malignant gliomas in adults," *Cancer*, 71:2585 (1993); and S. Diete et al., "Sex differences in length of survival with malignant astrocytoma, but not with glioblastoma," *J. Neurooncol.*, 53:47 (2001). Thus, there exists a need in the art for a novel therapy for GBM.

Cancer vaccines represent one such therapy for GBM. See, e.g. R. P. Glick et al., "Intracerebral versus subcutaneous immunization with allogeneic fibroblasts genetically engineered to secrete interleukin-2 in the treatment of central nervous system glioma and melanoma," *Neurosurg.*, 41:898 (1997); L. M. Liau et al., "Treatment of intracranial gliomas with bone marrow-derived dendritic cells pulsed with tumor antigens," *J. Neurosurg.*, 90:1115 (1999); and J. S. Yu et al., "vaccination of malignant glioma patients with peptide-pulsed DC elicits systemic cytotoxicity and intracranial T-cell infiltration," *Cancer Res.*, 61:842 (2001). The clinical efficacy of therapeutic vaccination for any human tumor, however, remains controversial because consistent tumor destruction or extended lifespan is not observed in most vaccinated cancer patients. See, e.g., S. A. Rosenberg et al., "Immunologic and therapeutic evaluation of a synthetic peptide vaccine for the treatment of patients with metastatic melanoma," *Nat. Med.*, 4:321 (1998); K. H. Lee et al., "Increased vaccine-specific T cell frequency after peptide based vaccination correlates with increased susceptibility to in vitro stimulation but does not lead to tumor regression," *J. Immunol.*, 163:6292 (1999); and L. Fong et al., "Altered peptide ligand vaccination with Flt3 ligand expanded DC for tumor immunotherapy," *Proc. Natl. Acad. Sci. USA*, 98:8809 (2001). In contrast, current cancer vaccines do reliably elicit tumor-reactive cytotoxic T lymphocytes ("CTL") in most patients. See, e.g., Rosenberg at 321; Lee at 6292; and B. Bodey et al., "Failure of cancer vaccines: the significant limitations of this approach to immunotherapy," *Anticancer Res.*, 20:2665 (2000). The reasons underlying the general clinical failure of cancer vaccines are unknown, but one possibility is that the kinetics of anti-tumor CTL killing in cancer patients may be too inefficient to keep pace with rapidly growing, mutating tumors in situ. Consistent with this notion, it was previously reported that therapeutic vaccination with autologous tumor antigen-pulsed DC is sufficient to enhance peripheral tumor-reactive CTL activity and CD8+ T cell infiltration into tumors in situ in GBM patients. See Yu et al. at 842. Nevertheless, improvements in overall patient survival were not apparent in this initial study.

Because CTL induce death in their cellular targets, it is not unreasonable to expect that inefficient CTL killing might either incompletely trigger death pathways in targeted tumor cells, or select for CTL-resistant tumor variants. In the first case, vaccine-elicited tumor-responsive CTL might fundamentally alter tumors by "priming" their death machinery. In the second case, such CTL could fundamentally alter tumor cell physiology and/or genetics. Both of these possibilities could, in theory, be exploited by additional therapeutic modalities. Therefore, the clinical insufficiency of cancer vaccines encourages the examination of synergy between vaccination and other therapies, particularly to the extent that such an examination might uncover a novel approach to cancer therapy.

BRIEF SUMMARY OF THE INVENTION

The invention relates to a novel treatment for cancer, and particularly cancers of the CNS; for example, cancers of the brain, such as GBM. In one embodiment, the invention includes a dual therapeutic approach to the treatment of cancer with at least one vaccination of DC and at least one course or regimen of chemotherapy. The two therapies may be administered concurrently with one another and/or with an initial vaccination preceding chemotherapy.

The dual therapeutic approach of the instant invention may further be implemented to beneficially influence the chemosensitivity of a mammal with cancer, including cancers of the CNS, by vaccinating the mammal with DC prior to and/or concurrently with administration of chemotherapy.

The DC used in connection with various embodiments of the invention may be autologous tumor antigen-presented DC or they may be "unprimed" DC. These cells can be prepared by a host of methodologies. Additionally, further therapeutic interventions may be implemented in connection with the inventive dual therapeutic approach, such as surgical resection of a tumor, radiation therapy and the like.

BRIEF DESCRIPTION OF THE DRAWINGS

FIG. 1 depicts tumor progression, in accordance with an embodiment of the present invention.

FIG. 5 depicts demographic and treatment parameters of GBM patient groups, in accordance with an embodiment of the present invention. Calculations of % 2-year survival and % 3-year survival illustrated therein excluded censored values.

FIG. 6 depicts vaccine trial composition and distinctions, in accordance with an embodiment of the present invention. CTL responsiveness illustrated therein was determined from five testable samples per trial.

FIG. 7 depicts chemotherapy use, in accordance with an embodiment of the present invention. Temozolomide standard dose, as illustrated therein, is 150-200 mg/m$^2$ qd×5 days every 28 days. Gliadel wafers are a timed-release encapsulation of 1,3-bis(2-chloroethyl)-1-nitrosourea ("BCNU"). What is meant by "CCNU" is 1-(2-chloroethyl)-3-cyclohexyl-1-nitrosourea.

DETAILED DESCRIPTION OF THE INVENTION

Figure 1A:
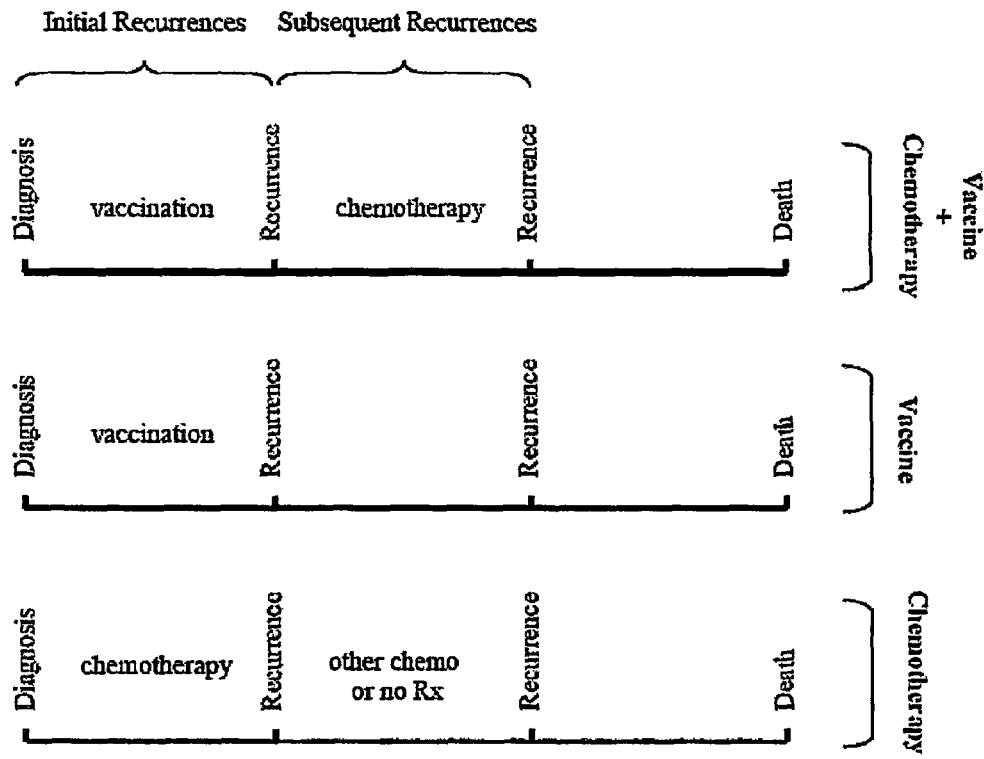
FIG. 1A illustrates tumor progression (recurrence) intervals monitored for each group of GBM patients. Progression times were monitored over intervals spanning vaccination or chemotherapy and subsequently thereafter.

All references cited herein are incorporated by reference as if fully set forth.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994); March, Advanced Organic Chemistry Reactions, Mechanisms and Structure 4th ed., J. Wiley & Sons (New York, N.Y. 1992); and Sambrook and Russel, Molecular Cloning: A Laboratory Manual 3rd ed., Cold Spring Harbor Laboratory Press (Cold Spring Harbor, N.Y. 2001) provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Alleviating" specific cancers and/or their pathology includes degrading a tumor, for example, breaking down the structural integrity or connective tissue of a tumor, such that the tumor size is reduced when compared to the tumor size before treatment. "Alleviating" metastasis of cancer includes reducing the rate at which the cancer spreads to other organs.

"Beneficial results" may include, but are in no way limited to, lessening or alleviating the severity of the disease condition, preventing the disease condition from worsening, curing the disease condition and prolonging a patient's life or life expectancy. The disease conditions may relate to or may be modulated by the central nervous system.

"Cancer" and "cancerous" refer to or describe the physiological condition in mammals that is typically characterized by unregulated cell growth. Examples of cancer include, but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer; including, but not limited to, astrocytomas, ependymal tumors, GBM and primitive neuroectodermal tumors.

"Chemotherapy," as used herein, refers to the use of chemicals, such as pharmaceuticals or drugs, in the treatment of a disease condition, such as cancer.

"Chemotherapeutic agents" denote particular chemicals, such as pharmaceuticals or drugs, which are used to effect chemotherapy.

"Conditions" and "disease conditions," as used herein, may include, but are in no way limited to any form of cancer; by way of example, astrocytomas, ependymal tumors, glioma, GBM and primitive neuroectodermal tumors.

"Curing" cancer includes degrading a tumor such that a tumor cannot be detected after treatment. The tumor may be reduced in size or become undetectable, for example, by atrophying from lack of blood supply or by being attacked or degraded by one or more components administered according to the invention.

"Mammal," as used herein, refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Treatment" and "treating," as used herein, refer to both therapeutic treatment and prophylactic or preventative measures, wherein the object is to prevent or slow down the targeted pathologic disease condition or disorder even if the treatment is ultimately unsuccessful. Those in need of treatment include those already with the disease condition as well as those prone to have or develop the disease condition or those in whom the disease condition is to be prevented. In tumor (i.e., cancer) treatment, a therapeutic agent (e.g., a chemotherapeutic agent) may directly decrease the pathology of tumor cells, or render the tumor cells more susceptible to treatment by other therapeutics, such as radiation therapy.

"Tumor," as used herein, refers to all neoplastic cell growth and proliferation, whether malignant or benign, and all precancerous and cancerous cells and tissues.

"Vaccine," as used herein (particularly with reference to "cancer vaccines"), refers to a preparation, typically in liquid or suspension form, of treated disease-producing microorganisms or their products, or of treated cells (e.g., dentritic cells harvested from the vaccine recipient), which are used to stimulate an immune response in the body so as to confer resistance to a disease condition or another beneficial result in the recipient.

The present invention is based, in part, on the surprising results obtained by the inventors in conducting a retrospective examination of the impact of therapeutic vaccination on the efficacy of conventional GBM chemotherapy. Progression rates and overall survival was compared among twelve vaccine-treated, thirteen chemotherapy-treated, and thirteen vaccine plus chemotherapy-treated de novo GBM patients. The results suggested that chemotherapy synergizes with previous therapeutic vaccination to generate a uniquely effective treatment that slows GBM progression and significantly extends patient survival relative to individual therapies. This represents the first evidence that a vaccine-based therapeutic approach may benefit a majority of cancer patients, and represents a novel treatment strategy that may substantially prolong GBM survival across a wide age range and relative to standard radiation plus chemotherapy. Additional independent evidence implicated anti-tumor T cells as influencing GBM chemosensitivity.

In accordance with an embodiment of the instant invention, a treatment for disease conditions, such as cancer, includes at least one therapeutic vaccination with a DC-based cancer vaccine in connection with at least one course of chemotherapy. This dual treatment may be administered to a mammal to alleviate, and potentially cure, a host of disease conditions; particularly cancer, and more particularly, cancers of the brain, such as GBM.

The cancer vaccine used in various embodiments of the instant invention may be selected from any dendritic cell ("DC")-based cancer vaccine, and can be administered by routine methods. The DC-based cancer vaccine may be administered concurrently with a course of chemotherapy and/or with an initial vaccination preceding chemotherapy. The DC may be autologous tumor antigen-presented DC that are "primed" ex vivo by conventional methods; for instance, the DC may be loaded with HLA-eluted peptides from cultured tumor cells or autologous tumor lysate. Alternatively, the DC may be delivered in an "unprimed" state and essentially primed in vivo, as described in U.S. patent application Ser. No. 10/251,148, filed Sep. 20, 2002, published as US 2004/0057935, the disclosure of which is incorporated by reference herein in its entirety. Use of "unprimed" DC may be particularly advantageous in instances where a tumor is surgically inoperable, where surgery is otherwise undesirable, or where no portion of the tumor can be retrieved for priming DC ex vivo against the tumor.

Briefly, "unprimed" DC include those that do not rely upon the acquisition of tumor tissue as a protein source, and the subsequent culturing therewith. In conventional methods, DC are primed ex vivo. Priming in this manner typically involves culturing the DC with the tumor cells against which they will subsequently be utilized; thereby providing the DC access to the tumor proteins and allowing the DC to process the associated antigens in preparation for presentation of the digested antigens to T-cells upon administration to a patient. However, in various embodiments of the present invention, DC may be delivered directly into a tumor bed or tumor region without first being primed ex vivo; the DC process the tumor antigens in vivo.

DC suitable for use in accordance with various embodiments of the present invention may be isolated or obtained from any tissue in which such cells are found, or may be otherwise cultured and provided. In particular, antigen-presenting DC may be used in accordance with the present invention. Such DC may be found, by way of example, in the bone marrow or PBMCs of a mammal., in the spleen of a mammal or in the skin of a mammal (i.e., Langerhan's cells, which possess certain qualities similar to that of DC, may be found in the skin and may further be employed in conjunction with the present invention, and are included within the scope of DC used herein). For instance, in one embodiment of the present invention, bone marrow may be harvested from a mammal and cultured in a medium that promotes the growth of DC. GM-CSF, IL-4 and/or other cytokines, growth factors and supplements may be included in this medium. After a suitable amount of time, clusters of DC may be harvested and/or subcultured and subsequently harvested for use in a cancer vaccine.

The DC-based cancer vaccine may be delivered to a recipient by any suitable delivery route, which may include, but is in no way limited to, injection, infuision, inoculation, direct surgical delivery, or any combination thereof In one embodiment of the present invention, the DC-based cancer vaccine may be administered to a mammal by direct inoculation via stereotactic surgery; a standard inoculation procedure known to those of skill in the art of neurosurgery. Moreover, the vaccine may be administered to a tumor itself, to a physiologic region in close proximity to the tumor or to a remote location within a mammal with respect to the target tumor or tumors.

The DC-based cancer vaccine of the present invention may include "primed" or "unprimed" DC in a pharmaceutical carrier. Any conventional pharmaceutical carrier may be used in accordance with the present invention, and an appropriate carrier may be selected by one of skill in the art by routine techniques. In one embodiment of the present invention, the pharmaceutical carrier is saline, although other carriers may be utilized depending upon the desired characteristics of the cancer vaccine. For example, one may formulate a cancer vaccine differently in order to account for different delivery techniques for the vaccine, physiological differences among patients (e.g., sex, weight, age, etc.), or different types of tumors (e.g., brain, breast, lung, etc.), among other factors. The DC-based cancer vaccine administered to a mammal in accordance with the present invention may be delivered in combination with any of a variety of additional substances and compounds; for example, any suitable carrier, vehicle, additive, excipient, pharmaceutical adjunct, or other suitable product.

The quantity of DC appropriate for administration to a patient as a cancer vaccine to effect the methods of the present invention and the most convenient route of such administration may be based upon a variety of factors, as may the formulation of the vaccine itself. Some of these factors may include, but are in no way limited to, the physical characteristics of the patient (e.g., age, weight, sex, etc.), the physical characteristics of the tumor (e.g., location, size, rate of growth, accessibility, etc.), and the extent to which other therapeutic methodologies (including chemotherapy, as well as beam radiation therapy) are being implemented in connection with an overall treatment regimen. Notwithstanding the variety of factors one should consider in implementing the methods of the present invention to treat a disease condition, a mammal may be administered with from about $10^5$ to about $10^7$ DC in from about 0.05 mL to about 0.30 mL saline in a single administration, in one embodiment of the present invention. Additional administrations may be effected, depending upon the above-described and other factors, such as the severity of tumor pathology. In one embodiment of the present invention, from about one to about five administrations of about $10\text{-}40\times10^6$ DC is performed at two-week intervals.

The chemotherapeutic agent used in connection with the present invention may be selected from any chemotherapeutic agent, as will be readily appreciated by one of skill in the art. Examples of such chemotherapeutic agents may include, but are in no way limited to, temozolomide, procarbazine, carboplatin, vincristine, BCNU, CCNU, thalidomide, irinotecan, isotretinoin (available from Hoffnan-LaRoche, Inc. under the tradename Accutane®), imatinib (available from Novartis Phanmaceuticals Corporation under the tradename Gleevec®), etoposide, cisplatin, daunombicin, doxorubicin, methotrexate, mercaptopurine, fluorouracil, hydroxyurea, vinblastine and pacitaxel. It will also be readily appreciated by those of skill in the art that, while a single chemotherapeutic agent may be administered to treat cancer in connection with various embodiments of the present invention, a wide array of combinations of chemotherapeutic agents may alternatively be administered in the treatment of cancer. Moreover, chemotherapeutic agents may be administered by any suitable delivery route, such as, without limitation, oral (PO), intravenous (IV), intrathecal (IT), intraarterial, intracavitary, intramuscular (IM), intralesional or topical.

In a further embodiment of the present invention, a kit is provided for the treatment of cancer in a mammnal. In one embodiment, the kit may be configured for cancers of the brain; for instance, for the treatment of GBM. The kit is useful for practicing the inventive method of treating disease conditions. The kit is an assemblage of materials or components, including at least one dose of a DC-based cancer vaccine and at least one dose of a chemotherapeutic agent. The exact nature of the components configured in the inventive kit depends on the particular DC-based cancer vaccine and chemotherapeutic regimens that are to be implemented. For instance, if the DC-based cancer vaccine used in accordance with a particular embodiment of the present invention is to include "primed" DC, then the inventive kit may include components that can be used in connection with priming a quantity of DC ex vivo. It should be readily apparent that, in embodiments of the present invention wherein the DC-based cancer vaccine is to include only "unprimed" DC, components used solely for priming the DC would not be necessary in the kit.

Instructions for use may be included with the kit. "Instructions for use" typically include a tangible expression describing the components of the kit and the treatment schedule, dosing and directions for administration of the DC-based cancer vaccine and chemotherapeutic agent or agents. In various embodiments, the instructions for use may describe the harvesting of DC from a mammal and/or a procedure to be implemented for priming the DC ex vivo. The kit may also contain other useful components, such as diluents, buffers, pharmaceutically acceptable carriers, specimen containers, syringes, stents, catheters, pipetting or measuring tools, and the like. The materials or components assembled in the kit can be provided to the practitioner stored in any convenient and suitable manner that preserves their operability and utility. For example the components can be in dissolved, dehydrated or lyophilized form. They can be provided at room, refrigerated or frozen temperatures.

The components are typically contained in suitable packaging material(s). As employed herein, the phrase "packaging material" refers to one or more physical structures used to house the contents of the kit. The packaging material is constructed by well known methods, preferably to provide a sterile, contaminant-free environment. The packaging materials employed in the kit are those customarily utilized in the field. As used herein, the term "package" refers to a suitable solid matrix or material such as glass, plastic, paper, foil, and the like, capable of holding the individual kit components. Thus, for example, a package can be a glass vial used to contain suitable quantities of a composition containing a chemotherapeutic agent. The packaging material generally has an external label which indicates the contents and/or purpose of the kit and/or its components.

EXAMPLE 1

Comparison Among Differentially Treated Patients

Figure 1B:
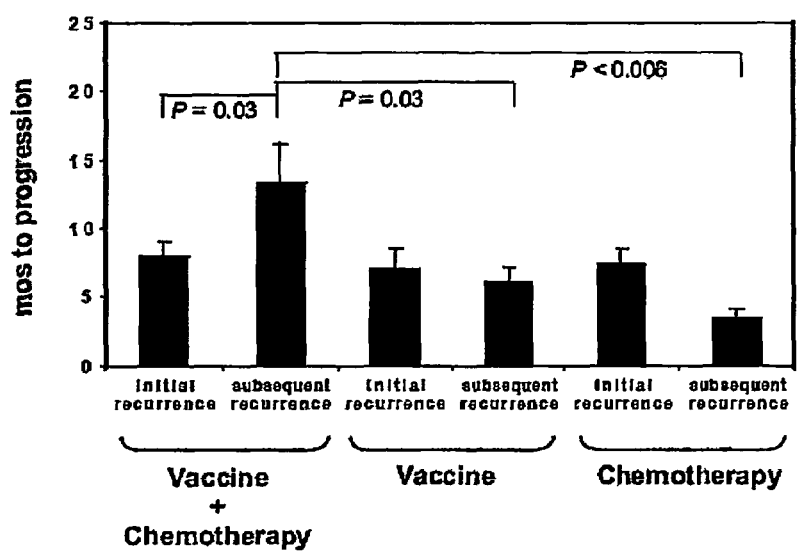
FIG. 1B illustrates time to tumor progression in vaccine, chemotherapy and vaccine+chemotherapy groups. Tumor progression was defined as the time from first diagnosis of brain tumor (de novo GBM in all cases) to the first new scan enhancement, if verified by subsequent scans or by histology, or time from diagnosis to death due to tumor progression. Mean times to tumor progression+standard error are shown for each group over specific intervals, as indicated. Significance (p values) were derived from double-sided paired (initial recurrence after vaccine vs. subsequent recurrence after chemotherapy in vaccine+chemotherapy group) or unpaired double-sided T tests (all other comparisons). Initial recurrence times were identical among all three groups ($P>0.6$). The small difference in subsequent recurrence times between vaccine and chemotherapy groups was not statistically significant ($P=0.07$).
Figure 2:
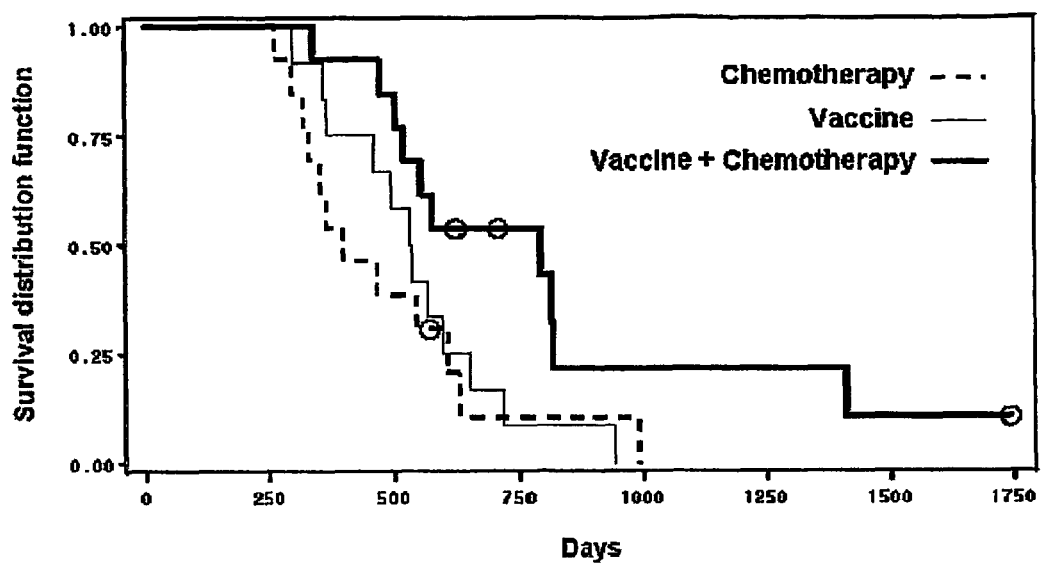
FIG. 2 depicts overall survival in vaccine, chemotherapy and vaccine+chemotherapy groups, in accordance with an embodiment of the present invention. Overall survival was defined as the time from first diagnosis of brain tumor (de novo GBM in all cases) to death due to tumor progression. Kaplan-Meyer survival plots with censored values in open circles are shown for each group. Broken line: chemotherapy group; solid thin line: vaccine group; solid bold line: vaccine+chemotherapy group. Survival of the vaccine group was identical to that of chemotherapy group ($p=0.7$, log-rank). Survival of vaccine+chemotherapy group was significantly greater relative to both survival in the other two groups ($p=0.047$, log-rank), and greater than survival in the chemotherapy group alone ($p=0.02$, log-rank). Survival of the vaccine group tended to be lower and was statistically different than that of the vaccine+chemotherapy group.

Newly-diagnosed de novo GBM patients (GBM did not arise from malignant progression of initially lower-grade gliomas) were enrolled into one of three vaccine studies or were administered chemotherapy alone, after surgical tumor resection and standard radiation therapy. As indicated in FIGS. 5 and 6, vaccinated ("vaccine" or "vaccine+chemotherapy") patients received at least three vaccinations with autologous tumor antigen-pulsed DC, starting approximately fifteen weeks post-surgery and five weeks post-radiation therapy, respectively. Patients receiving chemotherapy alone ("chemotherapy" patients) were treated (with surgery, radiation and chemotherapy) over the same time interval as vaccinated patients, as depicted in FIG. 7. Serial MRI scans were performed every 2-3 months in all patients. Tumor progression and overall survival among vaccine, chemotherapy and vaccine+chemotherapy groups were determined and compared, as illustrated in FIGS. 1 and 2.

Treatment and demographic parameters, including the extent of non-survivors, surgery before or after vaccination (where appropriate), chemotherapy before vaccination (where appropriate), gender and age were not significantly different among the relevant groups, as shown in FIG. 5. In addition, Karnofsky performance status ("KPS") was not significantly different between vaccine and vaccine+chemotherapy patient groups (FIG. 5). Inclusion criteria for vaccinated de novo GBM patients, the patient subgroup common among the three vaccine trials, were identical in the three vaccine trials (FIG. 6). Similarly, anti-tumor immune response rates were similar for the three vaccine trials (FIG. 6), suggesting that differences in antigen source and/or vaccine dosing among individual vaccine trials did not substantially impact their immunological efficacy. Moreover, vaccine, vaccine+chemotherapy and chemotherapy patients exhibited identical recurrence times following vaccination (FIG. 1), indicating a lack of inherent bias in tumor clinical behavior among all three groups after initial treatment.

Only the extent of surgical resection differed significantly between the patient groups, with all vaccinated patients receiving image-complete resections and a portion of chemotherapy patients receiving partial resections. This particular bias was expected to produce longer survival selectively in vaccine relative to chemotherapy groups. Surprisingly, and quite to the contrary, mean times to progression and overall survival of chemotherapy patients was similar to those in previous reports (See, e.g., Stupp et al. at 779) and did not differ significantly from those of vaccinated patients (FIGS. 1, 2 & 6). Thus, therapeutic vaccination by itself failed to significantly slow progression or prolong survival relative to conventional GBM chemotherapy (P=0.7, log-rank). These results suggested that anti-tumor immunity was either inefficiently induced or that GBM tumors were inherently resistant to vaccine-elicited immune destruction alone. Because efficient induction of anti-tumor CTL responses by this vaccine methodology was previously demonstrated (See Yu et al. at 842), the latter possibility appeared most likely.

EXAMPLE 2

Effect of Vaccination on Chemotherapeutic Treatment of GBM Tumors

To determine if vaccination was capable of eliciting more subtle affects on GBM tumors, the inventors examined whether vaccination could alter GBM sensitivity to subsequent chemotherapy. GBM patients receiving chemotherapy after vaccination enjoyed significantly prolonged tumor progression relative to those receiving vaccination or chemotherapy alone. Similarly, GBM patients receiving chemotherapy after vaccination exhibited significantly prolonged survival relative to those receiving either treatment individually. The possibility that an inadvertent selection bias resulted in inherently slower progressing tumors in patients receiving chemotherapy after vaccination is inconsistent with the statistically identical initial progression times (i.e., after initial vaccination or chemotherapy) among all three groups of patients ("vaccine", "chemotherapy" and "vaccine+chemotherapy"): tumors behaved the same, clinically, regardless of initial vaccination or chemotherapy, and slowed tumor progression was unique to the period of chemotherapy after vaccination. In addition, the two groups of vaccinated patients were statistically identical in terms of all other treatment parameters, including number of craniotomies, radiation, SRS and chemotherapy prior to vaccination, and exhibited similar Karnofsky performance scores after vaccine therapy.

Importantly, 2-, 3- and 4-year survival was also unique for patients receiving chemotherapy after vaccination. Whereas chemotherapy or vaccination alone resulted in 2-year survival within the established range for GBM (8%; FIG. 5), post-vaccination chemotherapy resulted in a substantial increase (42%; FIG. 5) in 2-year survivors (P<0.05; binomial distribution). Similarly, no 3-year or 4-year survivors were evident after chemotherapy or vaccination alone, but such survivors persisted in post-vaccine chemotherapy patients (P<0.01 for 3-year survivors; binomial distribution).

Finally, objective (>50%) regression of the entire tumor mass was observed in three of thirteen vaccine+chemotherapy patients and this occurred only after initiation of post-vaccine chemotherapy. A similar regression was also observed in a single grade III malignant glioma patient receiving chemotherapy after vaccination (data not shown). Such dramatic regression of de novo GBM was unique to this group and is unknown in the literature, although a single example of partial regression in a recurrent GBM following post-vaccine chemotherapy has recently been reported. See H. Okada et al., "Autologous glioma cell vaccine admixed with interleukin-4 gene transfected fibroblasts in the treatment of recurrent glioblastoma: preliminary observations in a patient with a favorable response to therapy," *J. Neuro-oncol.*, 64:13 (2003). In that report, however, rapid tumor recurrence, as judged by increased tumor on imaging studies, clearly occurred following vaccination, but was discounted to favor the notion that regression was related to vaccination itself. In this context, it is significant that tumor recurrence in all vaccinated patients in the current study was determined by increased tumor imaging on MRI scans. Moreover, 33% (4/12) of vaccine patients and 46% (6/13) of vaccine+chemotherapy patients were biopsied upon observation of post-vaccine increases in tumor imaging, with all exhibiting histologically verified recurrent tumor. This suggests that apparent increases in tumor imaging in our study were not due to vaccine-induced inflammatory responses and instead generally reflected bona fide tumor recurrence. This suggests that the specific therapeutic regimen of chemotherapy after vaccination, rather than vaccination alone, elicited the tumor regressions. In any case, this is the first demonstration of objective regression of entire tumor mass in any adoptive immunotherapy setting, as well as in the treatment of GBM generally.

The inventors' studies support the notion that clinical outcome is significantly improved by the specific combination and sequence of vaccination plus chemotherapy in GBM patients. Stated more generally, it is believed that anti-tumor immunity directly impacts GBM chemosensitivity. Vaccinated patients receiving subsequent chemotherapy exhibited significantly delayed tumor progression and longer survival relative to those receiving vaccinations without subsequent chemotherapy or to those receiving chemotherapy alone. Improved clinical outcome appeared dependent on the specific combination and sequence of therapeutic vaccination followed by chemotherapy. These observations suggest a substantial therapeutic slowing of GBM progression and extension of overall survival for GBM patients. These clinical benefits appeared to markedly surpass those in previous vaccine studies as well as those in even the most hopeful analyses of GBM chemotherapy. See, e.g., Stupp et al. at 779. Moreover, the more favorable clinical outcome conferred by post-vaccine chemotherapy did not appear to be confined to younger subgroups of patients. As such, this supports the notion that this specific treatment combination conferred clinical improvement to a majority of treated cancer patients, which is believed to be unique for a vaccine-based therapy.

EXAMPLE 3

CD8+ TREC Correlation with Increased Tumor Progression Time

Figure 4:
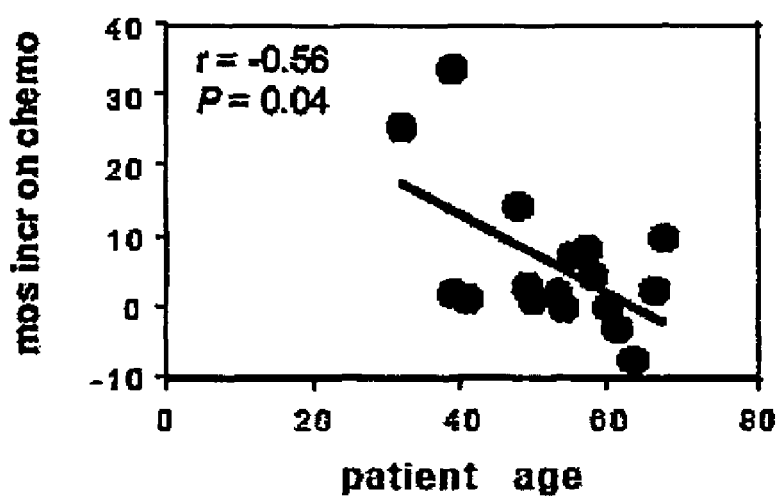
FIG. 4 illustrates that CD8+ T cell receptor excision circles ("TRECs") are strongly associated with chemotherapeutic responses following vaccination, in accordance with an embodiment of the present invention. The increase in time to tumor progression in months (y-axis) was correlated in the same GBM patients with: (A) TRECs quantified within 50,000 purified CD8+ T cells from peripheral blood mononuclear cells ("PBMC") collected at the time of surgery, or (B) patient age. Data were derived from all vaccinated GBM patients for whom chemotherapeutic response and TREC results (n=13) or age (n=17) were available. A related parameter, time to tumor progression after chemotherapy divided by time to tumor progression after vaccination, also correlated significantly with CD8+ TRECs ($r=0.73$; $P<0.01$), but failed to do so with patient age ($r=-0.40$; $P>0.05$).
Figure 4:
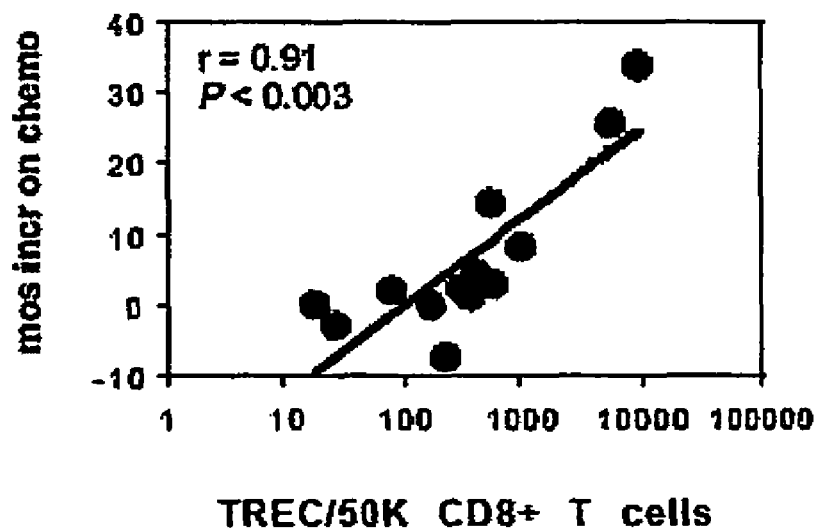

Thymic production of CD8+ T cells is accurately reflected by the concentration of TRECs in purified T cells. See, e.g., D. C. Douek et al., "Assessment of thymic output in adults after hematopoietic stem-cell transplantation and prediction of T-cell reconstitution," The Lancet, 355:1875 (2000); D. C. Douek et al., "Changes in thymic function with age and during the treatment of HIV infection," Nature, 396:690 (1998); and B. D. Jamieson et al., "Generation of functional thymocytes in the human adult," Immunity, 10:569 (1999). Moreover, thymic production of CD8+ T cells accounts for age-dependent glioma prognosis and outcome and predominantly influences vaccine-induced anti-tumor responses in GBM patients. See C. J. Wheeler et al., "Thymic CD8+ T cell production strongly influences tumor antigen recognition and age-dependent glioma mortality," J. Immunol., 171(9):4927 (2003). The inventors surmised that a direct influence of anti-tumor immunity on GBM chemosensitivity, itself an age-dependent phenomenon (See Fine et al. at 2585), would be reflected by a dominant relationship between CD8+ TRECs and chemotherapeutic responsiveness within the same GBM patients. Accordingly, TREC content within purified CD8+ T cells dominantly correlated with the increase in tumor recurrence times following post-vaccine chemotherapy. This relationship was not simply a function of an independent influence of age on chemosensitivity and thymic production of CD8+ T cells, because the strength and significance of this correlation surpassed that between increased recurrence times following post-vaccine chemotherapy and patient age (FIG. 4).

The close relationship between thymus products and glioma outcome is a direct result of CD8+ T cell production and/or function. See Wheeler et al. at 4927. Thus, the dominant relationship between CD8+ TRECs and prolonged progression times following post-vaccine chemotherapy suggests that clinical responsiveness to chemotherapy is similarly impacted by production and/or function of newly emigrated CD8+ T cells. Because levels of such T cells were shown to predominantly mediate anti-tumor immune responsiveness following vaccination of GBM patients (Id.), this constitutes independent validation of the notion that anti-tumor immunity impacts GBM chemosensitivity.

Taken together, although not wishing to be bound by any particular theory, these findings suggest that GBM tumors are recognized and acted on in situ by cellular immune components. Overall, such activity may result in fundamental alteration of GBM tumors that renders them increasingly susceptible to DNA damaging chemotherapy, despite the inability of vaccination by itself to confer overt clinical benefits to patients.

Furthermore, both clinical outcome and chemotherapeutic responsiveness are known to be age-dependent processes in gliomas generally. See, e.g., W. J. J. Curran at 690; Fine at 2585; and K. L. Chandler et al., "Long-term survival in patients with glioblastoma multiforme," Neurosurg., 32:716 (1993). Age-dependent glioma clinical outcome is critically impacted by the production of CD8+ T cells in the thymus in mice and a directly related parameter, TREC concentration within CD8+ T cells, accounts entirely for age-dependent prognosis in GBM patients. See Wheeler et al. at 4927. This raises the possibility of a similar immune impact on additional age-dependent properties of GBM, such as responsiveness to chemotherapy. In support of this, the inventors observed a robust correlation between CD8+ TRECs and GBM responsiveness to post-vaccine chemotherapy that surpassed that between age and responsiveness to chemotherapy. Thus, a particular cellular immune parameter appears to not only account for the strongest prognostic factor in GBM (i.e., age), but also appears to be closely linked to chemotherapeutic responsiveness of these tumors as well. Moreover, because age is the single most dominant factor influencing the outcome of most human tumors, establishing the generality of such an immune impact on distinct tumors could substantially broaden clinical expectations associated with immune-based cancer therapies. In this context, it will be additionally important to determine whether cellular immune processes similarly influence clinical outcome and chemotherapeutic efficacy in distinct human tumors.

EXAMPLE 4

Patients and Clinical Parameters

Figure 3:
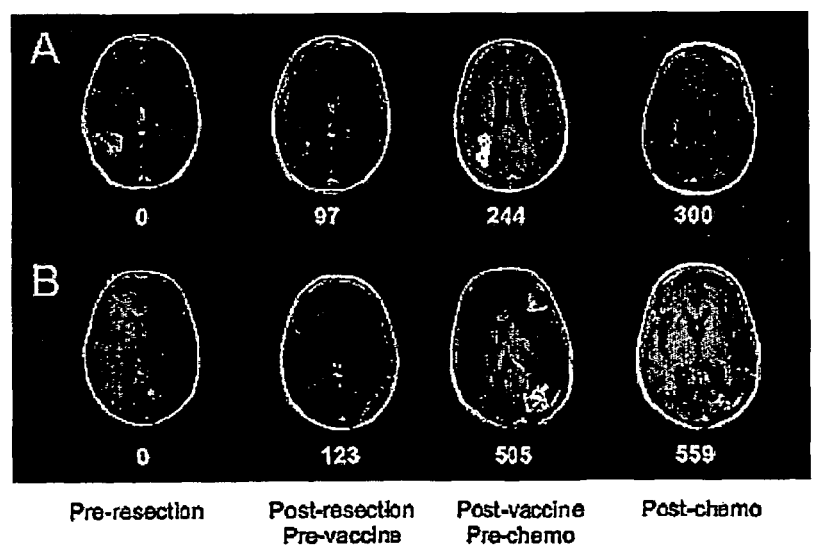
FIG. 3 depicts tumor regression following post-vaccine chemotherapy, in accordance with an embodiment of the present invention. Relative days after diagnosis are represented by numbers under individual MRI scans, with individual patients' scans in each row. Patient A recurred 82 days after vaccine initiation; patient B recurred 147 days after vaccine initiation, was treated surgically, and recurred 227 additional days (374 days total) after vaccine initiation. An additional patient suffering tumor recurrence 35 days after vaccine initiation and treated with subsequent chemotherapy experienced objective tumor regression, but a complete array of images was not available for this individual. All scans except the pre-resection scan for patient B were performed post-contrast enhancement with gadolinium. Two of the three patients exhibiting objective tumor regression survived more than two years (730 days) post-diagnosis.

All patients suffered from newly-diagnosed GBM (55 yrs average, 32-78 range) and provided informed consent to treatments and associated monitoring. Patients in the "vaccine group" underwent craniotomy (five patients underwent one craniotomy prior to receiving vaccine therapy, six underwent two craniotomies, and one patient underwent four craniotomies prior to receiving vaccine therapy). All of these patients received a course of radiation prior to vaccination. Four patients in this group also received chemotherapy and one patient received stereotactic radiosurgery ("SRS") prior to vaccination. After vaccination, five of these patients underwent another craniotomy, and three received additional SRS. None received chemotherapy following vaccination. All patients in the "chemotherapy group" underwent craniotomy, radiation and chemotherapy. Six of these patients underwent a second craniotomy, and five patients received additional SRS. Of note, the longest overall survivor in this group (991 days) suffered from post-operative intracranial abscess requiring multiple surgical procedures for drainage. Intracranial infections in malignant glioma patients are associated with prolonged survival and have been proposed to initiate an anti-tumor immune response. See A. P. J. Bowles et al., "Long-term remission of malignant brain tumors after intracranial infections: a report of four cases," *Neurosurgery*, 44:636 (1999). Patients in the "vaccine and chemotherapy group" underwent craniotomy (eight patients underwent one craniotomy and five underwent two craniotomies) prior to receiving the vaccine therapy. All of these patients received radiation therapy. Five patients received additional chemotherapy and three received SRS. Following vaccination, six of these patients underwent another craniotomy, and five received SRS. Al patients received chemotherapy following vaccination at the time of tumor progression. Notably, a single patient in this group (surviving>730 days and depicted in FIG. 3B) experienced a cutaneous glioblastoma with single lymph node involvement prior to vaccination and at the site of irradiated tumor cell inoculation for DTH testing. These two tumors were removed surgically approximately one year prior to chemotherapy and did not recur.

Vaccinated patients were steroid-free during blood collection and vaccinations were administered as described in Yu at 842. Patients received three vaccines, two weeks apart, of 10-40×10$^6$ autologous DC loaded with either HLA7 eluted peptides from cultured tumor cells or 150 μg/ml autologous tumor freeze-thaw lysate, starting approximately fifteen weeks post-surgery. A fourth identical vaccination followed six weeks later only in phase II trial patients (12 of 25). Serial MRI scans were performed every 2 to 3 months for all patients.

EXAMPLE 5

Cell Isolation and Lysis

PBMC were prepared with Ficoll from patients' blood obtained at the time of surgery and/or from banked leukaphereses. CD4+ and CD8+ T cells were purified from PBMC using MACS bead separation (obtained from Miltenyi Biotec; Auburn, Calif.). 10$^7$ CD4+ or CD8+ cells/ml were prepared for quantitative real-time PCR ("qPCR") by lysis in 100 μg/mL proteinase K (obtained fro Boehringer; Indianapolis, Ind.) 1 hr, 56° C., with inactivation at 95° C., 10 min.

EXAMPLE 6

TREC Quantification

TRECs were quantified in duplicate or triplicate by qPCR using the 5' nuclease (TaqMan) method as described in D. C. Douek et al., "Assessment of thymic output in adults after hematopoietic stem-cell transplantation and prediction of T-cell reconstitution," *The Lancet*, 355:1875 (2000), and detected on an iCycler system (obtained from BioRad; Hercules, Calif.). qPCR was performed on 5 μL cell lysate (from 50,000 cells) with the primers depicted in Table 1 (probe was obtained from MegaBases; Chicago, Ill.).

TABLE 1

| Primers Used in qPCR | | |
|---|---|---|
| Forward | 5'-CACATCCCTTTCAACCATGCT-3' | SEQ ID NO. 1 |
| Reverse | 5'-GCCAGCTGCAGGGTTTAGG-3' | SEQ ID NO. 2 |
| 5' FAM/3' TAMRA Probe | 5'-ACACCTCTGGTTTTTGTAAAGGTG CCCACT-3' | SEQ ID NO. 3 |

PCR reactions including 0.5 U Platinum Taq (obtained from Gibco; Grand Island, N.Y.), 3.5 mM MgCl$_2$, 0.2 mM dNTPs, 500 nM of each primer, 150 nM probe, were amplified at 95° C. for 5 minutes, 95° C. for 30 seconds, and 60° C. for 1 minute for 45 cycles. Control β-actin reactions were performed to ensure nucleic acid content and negative samples were excluded from further analysis. TREC values were adjusted for T cell purity.

EXAMPLE 5

Statistical Analyses

Statistical analyses included 2-tailed Mann-Whitney logrank tests for disease-free and overall survival, binomial distribution probability, and Pearson's correlation coefficients (r values) calculated with SAS and Excel software. Binomial distributions were determined for 2-year and 3-year survival frequencies between vaccine+chemotherapy and other (vaccine or chemotherapy) patient groups.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A method for treating a glioma in a mammal, the method comprising:
   (a) administering at least one vaccination of dendritic cells ("DC") to said mammal suffering from a glioma, wherein the at least one vaccination of DC comprises autologous DC that present autologous glioma antigens; and
   (b) after glioma recurrence following (a), administering a regimen of chemotherapy to said mammal, wherein said regimen of chemotherapy includes the administration of at least one chemotherapeutic agent selected from the group consisting of temozolomide, procarbazine, vincristine, BCNU, CCNU, thalidomide, irinotecan, isotretinoin, imatinib, etoposide, and combinations thereof.

2. The method of claim 1, wherein administering said at least one vaccination further comprises administering at least three vaccinations of DC.

3. The method of claim 1, wherein each of said at least one vaccination of DC comprises from about $10^5$ to about $10^7$ DC.

4. The method of claim 1, wherein each of said at least one vaccination of DC comprises about $10 \times 10^6$ to about $40 \times 10^6$ DC.

5. The method of claim 1, wherein said glioma is glioblastoma multiforme.

6. The method of claim 1, wherein said mammal is a human.

7. The method of claim 1, wherein the DC are primed ex vivo with autologous glioma cells.

8. The method of claim 7, wherein administering said at least one vaccination of DC comprises administering at least three vaccinations of DC.

9. The method of claim 7, wherein each vaccination of DC comprises from about $10^5$ to about $10^7$ DC.

10. The method of claim 7, wherein each vaccination of DC comprises about $10 \times 10^6$ to about $40 \times 10^6$ DC.

11. The method of claim 7, wherein said glioma is glioblastoma multiforme.

12. The method of claim 7, wherein said mammal is a human.

* * * * *